United States Patent [19]

Drent

[11] Patent Number: 5,091,587

[45] Date of Patent: Feb. 25, 1992

[54] PROCESS FOR THE PREPARATION OF KETONES

[75] Inventor: Eit Drent, Amsterdam, Netherlands

[73] Assignee: Shell Oil Company, Houston, Tex.

[21] Appl. No.: 615,755

[22] Filed: Nov. 19, 1990

[30] Foreign Application Priority Data

May 14, 1990 [GB] United Kingdom ............... 9010785

[51] Int. Cl.[5] ............................................. C07C 45/42
[52] U.S. Cl. .................. 568/408; 568/365; 568/309
[58] Field of Search ............... 568/409, 365, 408, 309

[56] References Cited

U.S. PATENT DOCUMENTS

| | | | |
|---|---|---|---|
| 3,836,553 | 7/1974 | Fenton | 260/409 |
| 4,117,016 | 9/1978 | Hughes | 260/593 R |
| 4,414,417 | 11/1983 | Mestroni et al. | 568/315 |
| 4,645,863 | 2/1987 | Rebafka et al. | 568/899 |

FOREIGN PATENT DOCUMENTS

| | | |
|---|---|---|
| 105663 | 9/1983 | European Pat. Off. . |
| 7334727 | 5/1969 | Japan . |
| 74035603 | 9/1974 | Japan . |
| 74048407 | 12/1974 | Japan . |
| 877143 | 3/1960 | United Kingdom . |
| 1530447 | 1/1975 | United Kingdom . |

OTHER PUBLICATIONS

Imai et al., "Transfer Hydrogenation and Transfer Hydrogenolysis VII. The Mechanism of Hydrogen Transfer from 2-Propanol to Olefins Catalyzed by Dihydridotetrakis-(Triphenylphosphine)Ruthenium(II)," Bulletin of the Chem. Soc. of Japan, vol. 48 (5), 1585–1589, 1975.

Ying-Rui et al., "Iridium Complex Catalyzed Hydrogen Transfer Reaction of Unsaturated Secondary Alcohols," Acta Chemica Sinica, 46 (1), 1988, pp. 93–95. (Article in Japanese).

Fragale et al., "Dehydrogenation of Sec-Alcohols to Ketones Promoted by Rhodium and Iridium Catalysts and Alkali," Journal of Molecular Catalysis, 5, 1978, pp. 65–73.

Primary Examiner—James H. Reamer

[57] ABSTRACT

A process for the preparation of ketones which comprises reacting a conjugated diolefin and water in the liquid phase in the presence of a catalyst system comprising:
a) a group VIII metal compound, and
b) a source of protons.

18 Claims, No Drawings

PROCESS FOR THE PREPARATION OF KETONES

FIELD OF THE INVENTION

The present invention relates to a process for the preparation of ketones and more in particular to a process for the preparation of ketones via the reaction of conjugated diolefins and water, and to the ketones thus prepared.

BACKGROUND OF THE INVENTION

Ketones are technically versatile and valuable products and are known to be prepared e.g. via the oxidation of secondary alcohols, the hydrogenation of unsaturated ketones, the decarboxylation of carboxylic acids and the hydration of non-terminal alkynes. Most of these reactions have in common that they use starting materials which as such are already valuable compounds, and are often prepared via processes which are conducted under stringent reaction conditions and/or necessitate laborious product isolation procedures.

A considerable improvement in the preparation of ketones would be achieved by employing a relatively cheap or more readily available feedstock or starting material. Such a process is known from Japanese applications 73-34728 and 74-48407 and relates to the reaction in the gas phase of an at least $C_5$-conjugated diolefin with water in the presence of an acidic catalyst and employing a water to conjugated diene weight ratio in the range of from 0.05:1 to 50:1. From the examples it appears that the yield of ketone is strongly dependent on and proportional to the water to diene ratio, a water to diene weight ratio of 41.5:1 still only resulting in a 48.7% yield of ketone based on isoprene supplied, while with a 2:1 weight ratio said yield is only 16%. The apparent requirement of such a large excess of water for a process which is conducted in the gas phase makes this process very unattractive from this energy consumption point of view. Not only does the evaporation of water require a lot of energy, but so will also the recovery of the ketone from the very dilute mixture. A further disadvantage of said process that it is restricted to conjugated diene having at least an isoprene configuration. Hence it can be concluded that there is considerable need for improvement in the preparation of ketones.

The problem underlying the present invention is developing a process for the preparation of ketones which does not have one or more of the disadvantages mentioned hereinbefore.

As a result of extensive research and experimentation, it has been found that ketones may be prepared from the reaction of conjugated diolefins with water in the presence of a catalyst system based on group VIII metals.

SUMMARY OF THE INVENTION

The invention provides therefore a process for the preparation of ketones which comprises reacting a conjugated diolefin and water in the liquid phase in the presence of a catalyst system comprising:
a) a group VIII metal compound, and
b) a source of protons.

DESCRIPTION OF THE PREFERRED EMBODIMENTS

In the context of the present invention, the term "source of protons" refers to protonic acids as well as to non-protonic acid compounds which generate protons in the presence of water.

Suitable catalyst components (a) include group VIII metal oxides, salts such as carboxylates, sulfates, sulfonates, nitrates, nitrites, halides, group VIII metal salts based on substituted acids such as halogenated carboxylic acids, e.g. trifluoroacetic acid, and halogenated sulfonic acids, e.g. trifluoromethanesulfonic acid; as well as group VIII metal complexes such as, for example, Group VIII metal phosphine complexes. Very good results have been obtained with group VIII metal acetylacetonates. Preferred such group VIII metal compounds are based on group VIII metals selected from the group consisting of ruthenium, rhodium, iridium and iron, with ruthenium being especially preferred.

The component (b) on which the catalyst system for the process of the present invention is based i.e. the proton source, is conveniently an acid having a $pk_a < 4$ (measured at 25° C. in aqueous solution). Suitable acids may be selected from a wide range of organic and inorganic acids, such as for example, hydrohalogenic acids, halogenoxy acids, carboxylic acids, substituted carboxylic acids such as haloacetic acids, orthophosphoric acid, pyrophosphoric acid, phosphonic acid, sulfonic acids, substituted sulfonic acids such as halosulfonic acids, sulfuric acids, fluorosilicic acids and ion-exchange resins; as well as acids containing polyoxy anions such as $H_4WO_4$ and $H_3[P(Mo_3O_{10})_4]$. Preferred organic and inorganic acids have a $pk_a < 2$ (measured at 25° C. in aqueous solution). Preferably, the component (b) comprises an acid selected from the group consisting of paratoluenesulfonic acid, sulfuric acid, perchloric acid, trifluoromethanesulfonic acid, perfluorocarboxylic acids and ion-exchange resins.

Generally the component b) will be employed in an at least equimolar quantity with respect to the Group VIII metal compound and preferably in an amount which is sufficient to provide a ratio of 3.5–60 eq $H^+$ per gram atom of group VIII metal.

In a preferred embodiment, the catalyst system for use in the process of the present invention also includes a ligand. In this context the term ligands refers to ligand compounds containing Group V(A) and VI(A) donor atoms.

Examples of compounds which may be employed as the ligand in the catalyst system for use in the process of the present invention are:
1) compounds of the general formula

wherein X and Y represent similar or different organic bridging groups, each having three or four atoms in the bridge, at least two of which are carbon atoms, such as 2,2'-bipyridine and derivatives thereof, such as 4,4'-dimethyl-2,2'-bipyridine, 4,4'-dichloro-2,2'-bipyridine, 4,4'-dimethoxy-2,2'-bipyridine, 2,2'-(3,6-dithiaoctamethylene) dipyridine, and 4,4'-dicarboxy-2,2'-bipyridine; 1,10-phenanthroline and derivatives thereof, such as 5-chloro-1,10-phenanthroline, 4,7-diphenyl-1,10-phenanthroline, 4,7-dimethyl-1,10-phenanthroline, 2,9-dichloro-1,10-phenanthroline, 5,6-dimethyl-1,10-phenanthroline, 1,10-phenanthroline-5-sulfonic acid, 4,7-diphenyl-1,10 phenanthroline disulfonic acid and 4,7-dimethyl-1,10-phenanthroline disulfonic acid sodium; 2,2'-biquinoline, 2-(2-pyridyl)benzimidazole, 3-(2-pyridyl)-5,6-diphenyl-1,2,4-triazine and 3-(2-pyridyl)-5,6-diphenyl-1,2,4-triazine-p,p'-disulfonic acid sodium, 2) compounds in which one phosphorus atom and one or more nitrogen atoms, which atoms bear no hydrogen, are present, and in which each one of the nitrogen atoms is connected to the phosphorus atom via an organic bridging group having at least one carbon atom in the bridge, such as
2-cyanoethyl-diphenylphosphine,
tris(2-cyanoethyl)phosphine,
2-pyridyl-diphenylphosphine,
bis(2-pyridyl)-phenylphosphine, and
3-(diphenylphosphino)-N,N-dimethyl-propion amide, 3) compounds of the general formula $R_1R_2M_1—R—M_2R_3R_4$, wherein $M_1$ is arsenic or antimony, $M_2$ is an element with an atomic number lower than that of $M_1$ and chosen from the group comprising of arsenic, phosphorus and nitrogen, $R_1$, $R_2$, $R_3$ and $R_4$ represent similar or different hydrocarbon groups which may or may not be substituted with polar groups and R represents a bivalent bridging group having 2-4 atoms in the bridge, such as
1-(diphenylphosphino)-3-(diphenylarsino) propane,
1-(diphenylphosphino)-3-(diphenylstibino) propane,
1-(diphenylarsino)-3-(dimethylamino) propane, and
1-(diphenylphosphino)-2-(diphenylarsino) ethane, 4) compounds of the general formula $R_1R_2M—R—MR_3R_4$, wherein M is an element chosen from the group made up of phosphorus, arsenic and antimony, and wherein $R_1$, $R_2$, $R_3$ and $R_4$ and R have the meanings given hereinbefore, such as
1,3-bis(diphenylarsino) propane
1,3-bis(diphenylphosphino) propane,
1,4-bis(diphenylphosphino) butane,
1,2-bis(diphenylphosphino) ethane,
1,3-bis[di(4-methoxyphenyl) phosphino] propane,
2-methyl-2-(diphenylphosphinomethyl)-1,3-bis(diphenylphosphino) propane and
$N,N,N^1,N^1$-tetrakis(diphenylphosphinomethyl) ethylenediamine, 5) compounds of general formula $R^1M^1—R—M^2—R^3$, wherein $M^1$ and $M^2$ are similar or different elements chosen from the group consisting of sulfur, selenium and tellurium, $R^1$ and $R^2$ are similar or different, optionally polar-substituted, hydrocarbon groups and R represents a bivalent bridging group containing at least two carbon atoms in the bridge, or $R^1$ and $M^1$ and/or $R^2$ and $M^2$ form a heterocyclic ring with a carbon atom of the bridging group R.

Preferred ligands for use in the process of the present invention are bidentate ligands and especially preferred are bidentate ligands of general formula I such as 2,2'-bipyridines and 1,10-phenanthrolines.

The ligand component will preferably be employed in an amount which corresponds with a ratio in the range of from about 0.5 moles to about 5 moles of ligand per gram atom of group VIII metal.

As mentioned hereinbefore, in the preferred catalyst system the component (b) will be present in an amount which is sufficient to provide a ratio in the range of from about 3.5-60 eq $H^+$ per gram atom of group VIII metal. When said catalyst system also includes a ligand, hereinafter referred as component (c), it should be realized that any non-coordinated ligand may reduce the overall acidity of the catalyst system. This may be remedied by a further addition of acid, in an amount sufficient to neutralize any non-coordinated ligand.

Although not essential for the process of the present invention, the use of an immobilized or supported ligand in the catalyst system, i.e. a ligand which has been anchored to a supporting material such as for example a silica, an alumina or a polymeric material, may also offer an advantage, e.g. for ease of catalyst removal or retrieval, or e.g. in the case of a continuous reaction procedure.

Catalyst systems obtainable by combining a ruthenium, iridium or rhodium metal compound, an acid having a $pk_a<4$ (measured at 25° C. in aqueous solution) and a ligand of general formula

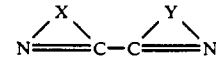

wherein X and Y represent similar or different organic bridging groups, each having three or four atoms in the bridge at least two of which are carbon atoms, are novel. Preferred such catalyst systems are based on a 1,10-phenanthroline or a 2,2'-bipyridine in view of their high activity.

The method used for preparing the catalyst system is not critical, and the catalyst may thus conveniently be prepared in situ in the reaction mixture by adding the components (a) and (b) or (a), (b) and (c) separately. Components (a) and (b) or (a), (b) and (c) may also be combined beforehand and subsequently added to the reactor, before, simultaneously with, or after the addition of one or more of the reactants. Combining the components (a), (b) and (c) may take place as such or in a suitable vehicle. In the preparation of the catalyst system for use in the process of the present invention, the component (b) will generally be employed in a quantity which is at least sufficient to provide an acidic catalyst system. Preferably, the component (b) will be employed in an amount which is sufficient to provide a ratio of about 3.5-60 eq $H^+$ per gram atom of group VIII metal in addition to an amount to overcome a possible neutralizing effect of any non-coordinated ligand compound.

Conjugated diolefins which may be used as starting material for the preparation of ketones according to the process of the present invention, include compounds of general formula

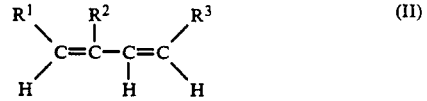

wherein $R^1$, $R^2$ and $R^3$ each independently represent hydrogen, an alkyl group or a mono- or polyolefinically unsaturated hydrocarbyl group; $R^1$ and $R^2$ may together form an organic bridging group containing at least 3 carbon atoms in the bridge. Examples of conjugated diolefins of general formula II are 1,3-butadiene, isoprene, 1,3-pentadiene, 1,3-hexadiene, 2,4-hexadiene, 1-vinyl-cyclopentene-1, 1-vinyl-cyclohexene-1. Other suitable conjugated diolefins include 1,3-cyclohexadiene and 1,3-cyclopentadiene.

Preferred conjugated diolefins are those wherein one of the olefinically unsaturated groups of the conjugated diolefin entity is an $\alpha$-olefin group, i.e. compounds of formula II wherein at least $R^1$ or $R^3$ represents hydrogen. Especially preferred conjugated diolefins are 1,3-butadiene and isoprene.

The process of the present invention may conveniently be conducted by contacting the conjugated diolefin, water and the catalyst in a suitable reactor at a temperature which will generally be in the range of from about 60° C. to about 200° C. and preferably in the range of from about 100° C. to about 170° C., and under autogenic pressure.

The amount of catalyst used with respect to the reactants is not critical and may vary over wide ranges and will generally correspond with a range of from about $10^{-7}$ to about $10^{-1}$ gram atom of group VIII metal per mole of conjugated diolefin converted to ketone and more particularly from about $10^{-5}$ to about $10^{-2}$ gram atom of metal per mole of diolefin.

The ratio wherein the conjugated diolefin and water may be used in the process of the present invention is not critical and may vary over wide ranges. Advantageously water may be used in a molar excess with respect to the conjugated diolefin. In view of the non-miscibility of water and the diolefins the reaction mixture may be a two-phase system, which two-phase system may eventually be converted into a single-phase system during the ketone synthesis.

Although the process of the present invention may be conducted as described hereinbefore, i.e. with a reaction medium essentially comprising diolefin, water and any reaction product formed, it may be advantageous to conduct said process in the presence of a solvent compound. Suitable solvents include hydrocarbon solvents, such as for example n-decane, as well as more polar solvents such as the dimethyl ether of diethylene glycol and the corresponding higher homologues.

When conducting the process of the present invention with a two-phase reaction medium, such as for example in the absence of a solvent or in the presence of an apolar solvent as mentioned hereinbefore, a beneficial effect on the ketone production was observed when substituting a more water-soluble ligand for the conventionally used ligand. Very good results having been obtained with modified 1,10-phenanthroline type compounds such as (4,7-diphenyl-1,10-phenanthroline) disulfonic acid sodium.

With the process of the present invention as described hereinbefore, it was observed that the gradual addition of the diolefin reactant during the reaction, rather than all of the diolefin being present in the reactor at the start of the reaction, had a beneficial influence on the ketone production. In a preferred embodiment of the present process, and wherein the gradual diolefin addition procedure may also be used, the diolefin may be employed as a mixture with other compounds—generally hydrocarbon compounds—which do not interfere with the reaction procedure. Preferred such conjugated diolefin-containing mixtures are selected cracked petroleum fractions. The compounds present in such a fraction or stream, generally have the same number of carbon atoms per molecule, but differ in degree of unsaturation. Especially preferred are the $C_4$-streams containing 1,3-butadiene together with other $C_4$-compounds such as butane, isobutene and 2-butene (cis- and trans-), and the corresponding $C_5$-stream containing isoprene as the diolefin compound. Employing such a conjugated diolefin cracked petroleum fraction in the process of the present invention, it has been demonstrated that a diolefin conversion to the corresponding ketone of 90% and higher may be obtained.

It will be appreciated that a process, as described hereinbefore, which allows the use of a multi-component feed mixture and wherein essentially only one of the components of the feed mixture is reacted and converted with a very high degree to the desired compound, i.e. a ketone, is of great value as part of a fully integrated process scheme wherein the different feed components may be selectively reacted and separated.

With the process of the present invention, the ketone reaction product may conveniently be isolated from the reaction mixture by known techniques such as distillation and extraction.

The invention will be further illustrated with the following examples for which the following information is provided. The examples are provided for illustrative purposes and are not to be construed as limiting the invention.

| Abbreviations used | |
|---|---|
| MEK: | Methyl ethyl ketone |
| acac: | Acetylacetonate |
| PTSA: | Paratoluenesulfonic acid |
| Ligand a: | 2,2'-bipyridine |
| Ligand b: | 6,6'-dimethoxy-2,2'-bipyridine |
| Ligand c: | 1,10-phenanthroline |
| Ligand d: | 2,9-dimethyl-1,10-phenanthroline |
| Ligand e: | 4,7-dimethyl-1,10-phenanthroline |
| Ligand f: | 5,6-dimethyl-1,10-phenanthroline |
| Ligand g: | 4,7-dimethyl-1,10-phenanthroline disulfonic acid sodium |
| Ligand h: | 2,2'-bis(4,5-dimethyl) imidazole |
| Ligand j: | 2,2',6',2''-terpyridine |
| Ligand k: | 2,2'-bithienyl |
| Ligand l: | 3-(2-pyridyl)-5,6-diphenyl-1,2,4-triazine |
| Ligand m: | 2,2'-(3,6-dithiaoctamethylene) bipyridine |
| Ligand n: | 3-(2-pyridyl)-5,6-diphenyl-1,2,4-triazine-p,p'-disulfonic acid |
| Ligand p: | 2-pyridyl-diphenylphosphine |
| Ligand q: | 4,4'-dimethyl-2,2'-bipyridine |
| Ligand r: | 2-(2-pyridyl)benzoimidazole |
| Ligand s: | 1,2-bis(diphenylphosphine)ethane |
| Amberlyst: | Amberlyst 252 H, a commercial ion-exchange resin ex Rohm and Haas |
| Diglyme: | Diethylene glycol dimethyl ether |

EXAMPLES 1-27

The appropriate amounts of water, solvent and catalyst components were introduced into a 250 ml stainless steel (Hastelloy C) autoclave equipped with a magnetic stirrer. Subsequently the reactor was closed and evacuated whereupon the conjugated diene was pumped in, and the reaction contents were heated to the desired temperature under autogenic pressure. After 5 hours reaction the reactor contents were cooled down to room temperature (20° C.).

Subsequently the reactor contents were analysed by gas liquid chromatography (G.L.C.). The relevant analytical data have been collected in Table I, which table also presents the type and amount of the compound employed in each example. The ketone yield is based on the amount of conjugated diolefin converted into the relevant ketone.

EXAMPLE 28

The following compounds were introduced into a reactor as described hereinbefore:

| 25 ml | diglyme |
| 40 ml | water |
| 1 mmol | Ru(acac)$_3$ |

| 2 mmol | 1,10-phenanthroline |
| 7 mmol | paratoluenesulfonic acid |

When the reactor contents had been heated to 155° C. under autogenic pressure, 1,3-butadiene was added to the reactor at a rate of 2 ml/h during 14 h. After the first hour of the 1,3-butadiene addition, the reactor temperature was lowered to 130° C. After a total reaction time of 16 h the reactor contents were cooled down to 20° C. G.L.C. analysis indicated the presence of 25 g of methyl ethyl ketone, which corresponded with a 1,3-butadiene conversion of 94% to methyl ethyl ketone.

EXAMPLE 29

The procedure of Example 28 was repeated with the exception that 25 ml of water was used, the reactor temperature was maintained at 155° C. and 1,3-butadiene was employed as a mixture having the following composition:

| 6.1 % m | butane |
| 19.3 % m | trans-2-butene |
| 4.5 % m | cis-2-butene |
| 26.0 % m | isobutene |
| 39.1 % m | 1,3-butadiene | which mixture was added to the reactor at a rate of 4 ml(liquid)/h during 2.5 h. After a total reaction time of 4.5 h the reactor contents were cooled down to 20° C. G.L.C. analysis indicated the presence of 5.7% m MEK in the liquid reaction mixture, corresponding with a 1,3-butadiene conversion of >90%.

EXAMPLE 30

The procedure of Example 29 was repeated but employing a C$_4$-stream containing 50% m 1,3-butadiene which was introduced into the reactor at a rate of 2 ml/h for 15 h. Furthermore the reaction was conducted in the absence of an additional solvent.

At the end of the reaction 15 ml of MEK was isolated from the reaction mixture, corresponding with a 1,3-butadiene conversion of 84%.

EXAMPLE 31

The procedure of Example 28 was repeated but employing 0.5 mmol Ru(acac)$_3$, 1 mmol of 1,10-phenanthroline, 45 ml of diglyme, 5 ml of water and isoprene (rate 1 ml/h during 5 h) and a total reaction time of 7 h at 155° C. This resulted in an isoprene conversion to methyl isopropyl ketone >95%.

TABLE I

| Example | Catalyst system Metal cpd mmol | Proton source mmol | Ligand mmol | Diolefin ml | Water ml | Solvent ml | Temp. °C. | Ketone % yield |
|---|---|---|---|---|---|---|---|---|
| 1 | Ru(acac)$_3$ 0.5 | CF$_3$COOH 27 | c 0.5 | Butadiene 10 | 5 | Decane 40 | 130 | 20 MEK |
| 2 | Ru(acac)$_3$ 0.5 | CF$_3$COOH 27 | a 0.5 | Butadiene 10 | 5 | Decane 40 | 130 | 15 MEK |
| 3 | Ru(acac)$_3$ 0.5 | CF$_3$COOH 27 | g 0.5 | Butadiene 10 | 10 | Decane 40 | 140 | 50 MEK |
| 4 | Ru(acac)$_3$ 0.5 | CF$_3$CH$_2$COOH 5* | g 0.5 | Butadiene 10 | 10 | Decane 40 | 140 | 80 MEK** |
| 5 | Ru(acac)$_3$ 1.0 | PTSA 5 | c 1.0 | Butadiene 10 | 10 | Diglyme 40 | 140 | 60 MEK |
| 6 | Ru(acac)$_3$ 1.0 | PTSA 13 | c 1.0 | Butadiene 10 | 25 | Diglyme 25 | 145 | 80 MEK |
| 7 | Ru(acac)$_3$ 1.0 | PTSA 4 | c 2.0 | Butadiene 10 | 25 | Diglyme 25 | 145 | 85 MEK |
| 8 | Ru(acac)$_3$ 0.5 | Amberlyst 2.5*** | c 0.5 | Butadiene 10 | 10 | Diglyme 40 | 130 | 10 MEK |
| 9 | Ru(acac)$_3$ 1.0 | H$_3$PO$_4$ 13 | c 1.0 | Butadiene 5 | 5 | Diglyme 40 | 145 | 15 MEK |
| 10 | Ru(acac)$_3$ 0.5 | CF$_3$COOH 27 | c 0.5 | Isoprene 5 | 5 | Diglyme 40 | 140 | 30 Methyl isopropyl ketone |
| 11 | Ru(acac)$_3$ 0.5 | CF$_3$COOH 27 | c 0.5 | 1,3-cyclo-hexadiene 10 | 5 | Decane 40 | 140 | 10 Cyclohexanone |
| 12 | Na$_3$IrCl$_6$ 1.0 | PTSA 13 | c 1.0 | Butadiene 5 | 5 | Diglyme 40 | 140 | 20 MEK |
| 13 | Ru(acac)$_3$ 1.0 | PTSA 13 | p 1.0 | Butadiene 5 | 25 | Diglyme 25 | 145 | 30 MEK |
| 14 | Ru(acac)$_3$ 1.0 | PTSA 13 | k 1.2 | Butadiene 10 | 25 | Diglyme 25 | 145 | 15 MEK |
| 15 | Ru(acac)$_3$ 1.0 | PTSA 13 | b 1.0 | Butadiene 5 | 25 | Diglyme 25 | 145 | 25 MEK |
| 16 | Ru(acac)$_3$ 1.0 | PTSA 13 | d 1.0 | Butadiene 5 | 25 | Diglyme 25 | 145 | 20 MEK |
| 17 | Ru(acac)$_3$ 1.0 | PTSA 13 | e 1.0 | Butadiene 5 | 25 | Diglyme 25 | 145 | 75 MEK |
| 18 | Ru(acac)$_3$ 1.0 | PTSA 13 | f 1.0 | Butadiene 5 | 25 | Diglyme 25 | 145 | 75 MEK |
| 19 | Ru(acac)$_3$ 1.0 | PTSA 13 | h 1.0 | Butadiene 5 | 25 | Diglyme 25 | 145 | 10 MEK |
| 20 | Ru(acac)$_3$ 1.0 | PTSA 13 | j 1.0 | Butadiene 5 | 25 | Diglyme 25 | 145 | 60 MEK |
| 21 | Ru(acac)$_3$ 1.0 | PTSA 13 | l 1.0 | Butadiene 5 | 25 | Diglyme 25 | 145 | 20 MEK |
| 22 | Ru(acac)$_3$ 1.0 | PTSA 13 | m 1.0 | Butadiene 5 | 25 | Diglyme 25 | 145 | 20 MEK |
| 23 | Ru(acac)$_3$ 1.0 | PTSA 13 | n 1.0 | Butadiene 5 | 25 | Diglyme 25 | 145 | 20 MEK |
| 24 | Ru(acac)$_3$ 1.0 | PTSA 13 | q 1.0 | Butadiene 5 | 25 | Diglyme 25 | 145 | 60 MEK |
| 25 | Ru(acac)$_3$ 1.0 | PTSA 13 | r 1.0 | Butadiene 5 | 25 | Diglyme 25 | 145 | 30 MEK |
| 26 | Ru(acac)$_3$ 1.0 | PTSA 13 | s 1.0 | Butadiene 5 | 25 | Diglyme 25 | 145 | 20 MEK |
| 27 | Ru(acac)$_3$ 0.5 | CF$_3$COOH 27 | — | Butadiene 10 | 5 | Decane 40 | 130 | 5 MEK |

*ml
**3 h reaction
***g

I claim:

1. A process for the preparation of ketones which comprises reacting at a temperature in the range of from about 60° C. to about 220° C. a conjugated diolefin of general formula

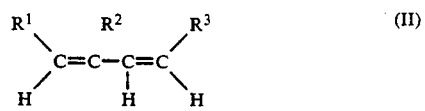

wherein $R^1$, $R^2$ and $R^3$ each independently represent hydrogen, an alkyl group or mono-or polyolefinically unsaturated hydrocarbyl group, and wherein $R^1$ and $R^2$ may together form an organic bridge group containing at least 3 carbon atoms in the bridge, and water in the liquid phase in the presence of a catalyst system comprising;

a) a Group VIII metal compound selected from the group consisting of Group VIII metal oxides, Group VIII metal salts and Group VIII metal complexes, and
b) a source of protons comprising an acid having a $pk_a<4$ (measured at 25° C. in aqueous solution).

2. The process of claim 1 wherein the group VIII metal is selected from the group consisting of ruthenium, rhodium, iridium and iron.

3. The process of claims 1 or 2, wherein the group VIII metal is ruthenium.

4. The process of claim 1 wherein the acid has a $pk_a<2$ (measured at 25° C. in aqueous solution).

5. The process of claims 1 or 2 wherein the proton source is an acid selected from the group of acids consisting of paratoluenesulfonic acid, sulfuric acid, perchloric acid, trifluoromethanesulfonic acid, perfluorocarboxylic acids and ion-exchange resins.

6. The process of claim 1 wherein the amount of catalyst component(b) is sufficient to provide a ratio of about 3.5 to about 60 equivalents of $H^+$ per gram atom of group VIII metal.

7. The process of claim 1 wherein the catalyst system additionally comprises a ligand.

8. The process of claim 7 wherein the ligand is a bidentate ligand.

9. The process of claim 8 wherein the bidentate ligand is a compound of general formula

 (I)

wherein X and Y represent similar or different organic bridging groups, each having three or four atoms in the bridge at least two of which are carbon atoms.

10. The process of claim 7 wherein said ligand is present in an amount which corresponds with a ratio of about 0.5 to about 5 moles of ligand per gram atom of group VIII metal.

11. The process of claim 1 wherein in general formula II at least one of $R^1$ or $R^3$ represent hydrogen.

12. The process of claim 11, wherein the conjugated diene is selected from 1,3-butadiene and isoprene.

13. The process of claim 12 wherein the amount of catalyst employed is in the range of from about $10^{-7}$ gram atom to about $10^{-1}$ gram atom of group VIII metal per mole of conjugated diolefin.

14. The process of claim 13 wherein the amount of catalyst employed is in the range of from about $10^{-5}$ gram atom to about $10^{-2}$ gram atom of group VIII metal per mole of conjugated diolefin.

15. The process of claim 1 wherein the reaction between water and diolefin is effected at a temperature in the range of from about 100° C. to about 170° C.

16. The process of claim 1 wherein the reaction between water and diolefin is conducted in the presence of a solvent.

17. The process of claim 1 wherein the conjugated diolefin is gradually added to the reactor during the reaction.

18. The process of claim 1 wherein the conjugated diolefin is employed as a mixture with other hydrocarbon compounds having the same number of carbon atoms per molecule as the diolefin, with a lesser degree of unsaturation.

* * * * *